United States Patent [19]
Frazier

[11] 4,215,983
[45] Aug. 5, 1980

[54] ORTHODONTIC HEADGEAR APPLIANCE SAFETY SYSTEM

[76] Inventor: Paul D. Frazier, 6709 Old Stage Rd., Rockville, Md. 20852

[21] Appl. No.: 703,828

[22] Filed: Jul. 9, 1976

[51] Int. Cl.² .............................................. A61C 3/00
[52] U.S. Cl. ........................................................ 433/5
[58] Field of Search ...................................... 32/14 D

[56] References Cited

U.S. PATENT DOCUMENTS

| | | | |
|---|---|---|---|
| 3,903,604 | 9/1975 | Sneed | 32/14 D |
| 3,997,971 | 12/1976 | Moss | 32/14 D |
| 4,115,921 | 9/1978 | Armstrong | 32/14 D |

FOREIGN PATENT DOCUMENTS

2641019  9/1976  Fed. Rep. of Germany .......... 32/14 D

OTHER PUBLICATIONS

American Journal of Orthodontics, Nov. 62, vol. #48, No. 11, p. 6.

Primary Examiner—Robert Peshock
Attorney, Agent, or Firm—Haight & Huard

[57] ABSTRACT

An orthodontic headgear appliance having a safety system which includes a release mechanism for the headgear tensioning apparatus, a system for selectively setting limits for free travel of the facebow and for activating a disconnecting system when a forward force on the facebow is still being applied when the travel limit is reached.

9 Claims, 9 Drawing Figures

ORTHODONTIC HEADGEAR APPLIANCE SAFETY SYSTEM

BACKGROUND OF THE INVENTION

Recent incidents in the field of orthodontics have made practitioners aware of safety hazards surrounding the use of various equipment. Especially potentially hazardous are extra-oral appliances, i.e., those worn outside the mouth or in conjunction with equipment outside the mouth. In particular, facebows and low and high pull headgear have been found to be a source of potential injury to the patient, since such appliances have heretofore been designed so that undesirable pulling of the facebow away from the patient's mouth "loads" the appliance in much the same manner as a slingshot. Additionally, if the ends of the inner bow are drawn sufficiently far forward, they will slip out of the buccal tubes usually employed to support them and become misaligned with the tube openings, thereby presenting themselves as a pair of pointed, dangerous protrusions. If the facebow is pulled out sufficiently, the ends of the inner bow may be in a position to do serious damage to the inner mouth, tongue, gums or even the lips, face and eyes. At least one such incident has been reported which resulted in blinding the patient.

Prior art solutions to the problem of eliminating dangers associated with undesired tampering with the facebow or undesirable pulling on the headgear tensioning means include various methods, depending upon the type of tensioning apparatus being used (spring, rubber band or elastic strap) and upon the individual preference of the orthodontist. One approach is to permanently tie the inner bow in place with steel ligature wire. This method presents some hygiene problems but causes more concern because undesired pulling could cause the facebow to be severly deformed. If the patient should continue wearing a deformed facebow, it could cause harm to the patient in addition to being detrimental to the intended orthodontic treatment.

Because of the obvious disadvantages and dangers of permanently affixing the inner bow to the buccal tubes, removal systems which avoid the dangers enumerated above are much more desirable. Several removable systems are presently available to the orthodontic practitioner, including but not limited to the following:

One removable headgear system, described in U.S. Pat. No. 3,903,604, uses two different devices for locking the inner bow into the buccal tube. These mechanisms appear to satisfy the requirement that the device be capable of selective removal by either the orthodontist or the patient; however, the apparatus described is complex, expensive to manufacture and does not permit adjusting the length of the inner bow members for different patients. This presents a significant manufacturing problem and an inventory problem for the practitioner, since a very large selection of sizes is required in order to accomodate the average size distribution of patients.

A second approach attempts to limit extension of the tensioning means. While theoretically intended to limit the travel of the inner bow members in the bucca tubes, the practical result is at best confinement of the inner bow members to the oral cavity. These devices are of limited value because they do not prohibit undesired removal of the inner bow members from the buccal tube; the serious danger of a "slingshot" effect caused by the tensioning means propelling the ends of the facebow into soft tissues of the oral cavity is thus not eliminated. The reason for the failure of these travel limiting devices is the fact that it is impossible to eliminate displacement of the soft tissues of the patient's neck or to control the angle of the patient's head. Both of these factors influence the amount of slack in the tensioning members of the device in relationship to their connection to the outer members of the facebow. These devices may actually be more dangerous because of the false sense of security they provide.

A third approach to assure safety of headgear devices by preventing undesired removal of the bow members is presently available to the profession and provides a breakaway mechanism between the tensioning means and the facebow. This particular mechanism is designed to function on a spring tensioning system, e.g. as described in U.S. Pat. No. 3,526,035, but is not directly adaptable to headgear using other elastic tensioning means. The major advantage of this safety means is that the "slingshot" effect and permanent damage to the semi-rigid portions of the apparatus are both effectively prevented. There are, however, major practical disadvantages associated with this system in addition to its applicability being limited to spring tensioned headgear. First, a large inventory of headgear is required because the system is designed to have a narrow, preset force range to insure proper functioning of the disconnect system. Second, the travel limiting system is not adjustable and provides such limited travel that disconnection may occur while attempting to engage the apparatus. Third, the force adjustment feature, in addition to having a narrow range, allows only discrete rather than continuous adjustments. Finally, the force module is not self-contained which necessitates the manufacture and assemblage of additional parts, making the unit considerably more expensive than non-safety versions of the same apparatus.

OBJECTS OF THE INVENTION

Accordingly, it is a general object of this invention to provide improved and safer orthodontic headgear appliances.

Another object of this invention is to provide safety disengaging devices for use with various types of headgear tensioning systems.

A further object of this invention is to provide stretch-limiting means for conventional elastic neckstrap headgear as well as rubber band tensioning neckstrap and headcap appliances.

An additional object of this invention is to provide improved means for adjusting and activating disconnecting devices for spring tensioned headgears.

Yet another object of this invention is to provide improved means for adjusting the force of spring tensioning headgear in conjunction with the safety disengaging means and to simplify their manufacture and use.

Other objects of the present invention will become apparent to those skilled in the art upon further study of the specification and appended claims.

SUMMARY OF THE INVENTION

Briefly, the above and other objects, features and advantages of the present invention are attained in one aspect thereof by providing an orthodontic headgear tensioning apparatus for use with an orthodontic facebow, comprising:

an elastic neckband;

means for limiting the expansion travel of the elastic neckband;

facebow coupling means securely attached to each end of the elastic neckband; and disconnect means normally connected between each of said coupling means and the facebow outer bow ends for disconnecting from said coupling means when a pulling force persists on the facebow after said travel limiting means has limited the expansion travel of the elastic neckband.

BRIEF DESCRIPTION OF THE DRAWINGS

The above and other objects, features and advantages of the present invention will become more fully apparent to those skilled in the art to which the invention pertains from the following Detailed Discussion, taken in conjunction with the annexed Drawings wherein like or corresponding reference characters refer to like or corresponding parts and in which.

DETAILED DISCUSSION

In accordance with the present invention, a disconnecting attachment system is provided which is designed to attach to the end of the facebow outer member providing means whereby, when used in conjunction with an elastic neckstrap equipped with standard metal end fasteners and a special stretch-limiting device, it will disconnect when improperly pulled. Since this disconnecting device is located at the end of the outer bow, it also conveniently functions in conjunction with rubber band tensioned force means equipped with a special stretch limiting device interposed between them and the non-elastic neckstrap or headcap and the facebow member.

Modifications of the above described attachment and disconnecting devices along with multiple improvements in the design, adjustment and safety features of spring tensioning devices are also provided.

The presently preferred devices of the present invention provide efficient and reliable means for assuring safely limited resilient neckstraps, rubber band biased neckstraps or headcap appliances. The travel limiting features are particularly important because of the necessity to activate the disconnecting mechanisms to prevent loading the headgear tensioning systems as dangerous slingshot weapons. Additionally, in association with the stretch limiting features, provision is made for disconnecting the tensioning system if it is improperly or inadvertently disengaged. In one variation, the attachment-disconnecting means is fixed to the headgear facebow outer member. An alternate disconnecting means to accomplish the same result is by use of a specially equipped intermediate attachment strap.

Figure 1:
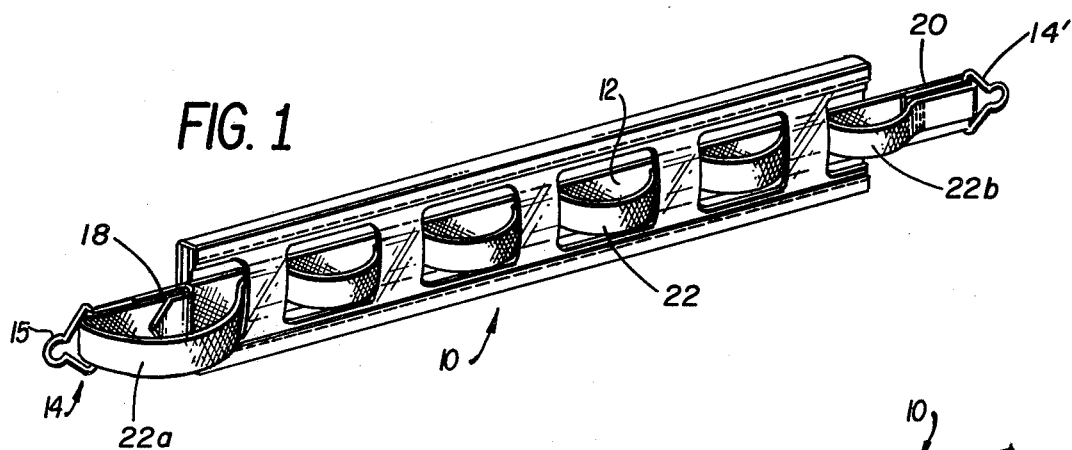
FIG. 1 is a perspective view of an elastic orthodontic headgear neckstrap embodying a presently preferred travel limiting means and adapted for one safety disconnect means of the present invention.
Figure 2:
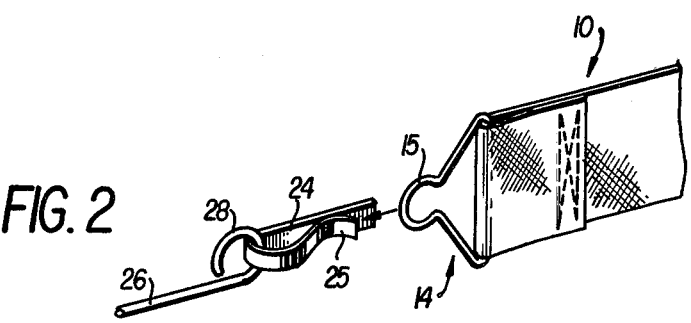
FIG. 2 is an enlarged perspective view of a safety disconnect means useful with the neckstrap of FIG. 1.
Figure 3:
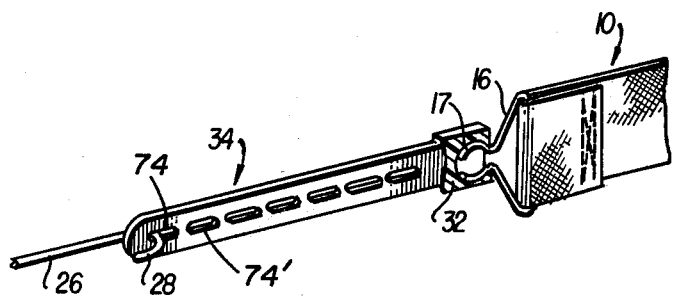
FIG. 3 is a perspective view, partially in cross-section, showing another safety disconnect means useful with the neckstrap of FIG. 1 attached to a travel limiting and tension adjustment means on an orthodontic appliance.

Referring now to the Drawings, FIG. 1 shows an orthodontic headgear neckstrap 10 which includes a strap 12 made of a resilient material, the ends of which are looped around connecting members 14 and 14' and attached to end members 18 and 20. It is understood that more than one adjustment member 18 may be used if desired. Member 18 is of a typical adjustment buckle configuration having projections which engage the strap material, preventing movement of the members. Connecting member 14 is of a standard conventional design having a terminal loop portion 15. Other designs may be used e.g. as shown in FIG. 3. Wherein member 16 is a specially designed resilient compression member having portion 17 which is designed to expand to lock and compress to disengage. Only one type connecting member will generally be used for a given application. A non-elastic stretch limiting strap 22 is located along neckstrap 10 and its ends 22a and 22b are looped around members 14 and 14' and attached in any suitable fashion to members 18 and 20. The connection of strap 22 to adjustment buckle 18 provides automatic adjustment when tension adjustment of elastic strap 12 is made. Strap 22 is designed so as to limit the stretch of resilient strap 12 so a disconnecting means designed to operate with connecting member 14 can operate, e.g. as shown in FIG. 2. The stretch-limiting system of this invention effectively controls travel distance of the facebow to which it is attached, thus providing a mechanism for activating the disconnecting devices in the event of improper, inadvertent or malicious pulling on either the facebow or strap portion of the apparatus.

FIG. 2 shows a disconnecting device 24 mounted through a hook 28 of a facebow outer arch 26 and is adapted to engage the loop 15 of metal fastener 14 on a standard resilient neckstrap 25, such neckstrap having attached a stretch-limiting strap as in FIG. 1. This system is particularly effective in providing a safety means; it is also convenient because it utilizes only the stretch-limiting system in conjunction with an otherwise standard elastic strap and the engaging and disconnecting means is conveniently attached to a standard facebow. There are no separate loose parts to be manipulated or misplaced.

FIG. 3 shows a disconnecting system designed to provide the same benefits as that of FIG. 2. Deformable portion 17 of member 16 is designed to fit within an opening which is formed in the end 32 (shown in cross-section) of an intermediate connecting strap 34 designed to receive portion 17 and to connect to the hook 28 of the outer bow 26. Strap 34 is provided with a series of longitudinally spaced holes 74, 74' therein for adjustment purposes. Strap 34 provides an additional means of adjusting tension on the facebow member 26 by selecting one of the holes of strap 34 for attachment to facebow hook 28. Strap 34 may be shortened to fit a particular patient.

The arrangement as in FIG. 3 also allows the neckstrap to stretch a certain amount until member 10 is taut. At this point, further stretching is prohibited and the shape of opening end 32 will compress portion 17 allowing it to slide out of the opening. The force necessary to pull connecting member 17 out of opening end 32 can be predetermined by the cross-sectional size of member 16, the shape of member 17 and the shape of connecting member opening end 32. Thus, if an inadvertent or malicious force is applied, the extraoral appliance will be disengaged, thereby preventing loading of the appliance as a dangerous device.

Figure 4:
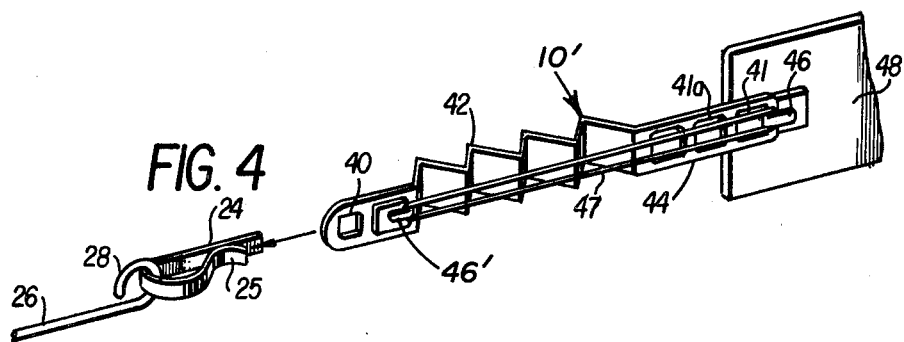
FIG. 4 is a perspective view of the safety disconnect means of FIG. 2 used with a neckstrap variation in which travel is limited by an inelastic accordian strap and tension is applied by a rubber band.

FIG. 4 shows another variation in which a disconnecting device 24 is attached directly to loop 28 of facebow outer arch 26. The connecting portion 25 is adapted to engage a hole 40 or other attachment means of the stretch-limiting strap 10' which in the version presented has an accordian-like pleated section 42 and flat portion 44. A hooking means 46 attached to a non-resilient neckstrap 48 engages one of a series of apertures 41, 41a in strap 10' for attachment of the flat portion 44. A second hooking means 46' is mounted on the front portion of strap 10'. An elastic module 47 is adapted to extend between the hooks to place tension on the facebow. In a variation of this device (not shown), the accordian feature may be omitted by elongating the holes 41, 41a to provide freedom for contracting by the elastic means 46 and to limit travel in the elastic expansion direction. When assembled on a patient, the apparatus so described will allow normal desirable rearward force and forward movement only until slack is removed from the system. Once taut, further force will cause disconnecting portion 25 to separate from aperture 40 or other attachment means of strap 10'. This embodiment and that described but not shown each provide an excellent means of assuring safety of rubber band tensioning neckstrap and headcap appliances.

A second group of devices shown in FIGS. 5, 6, 8 and 9 provides distinct advantages over existing spring biased headgear systems. In these embodiments, means are provided for infinitely adjusting the spring tension and subsequently the force on the facebow; the limitations of factory predetermined force ranges are thereby eliminated. Additionally, travel limiting means are provided which may also be adjusted as desired, thus again eliminating factory set travel limits. The former feature especially serves to eliminate the practitioner's need for keeping a large inventory on hand in order to satisfy commonly encountered force selection requirements. A convenient intermediate attachment means is provided and one variation of such means is also shown in FIG. 7. A variation of the force selection means is also provided in FIG. 5. These force modules are self-contained units, eliminating the need to build them in conjunction with supporting members.

Figure 6:
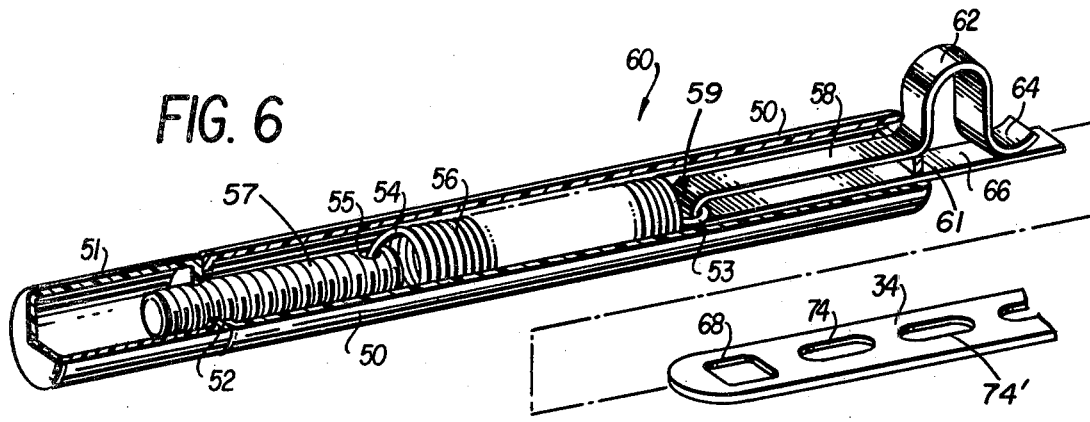
FIG. 6 is a partially cutaway perspective view of a continuously variable tension adjustment device combined with a safety disconnect device of the present invention.
Figure 7:
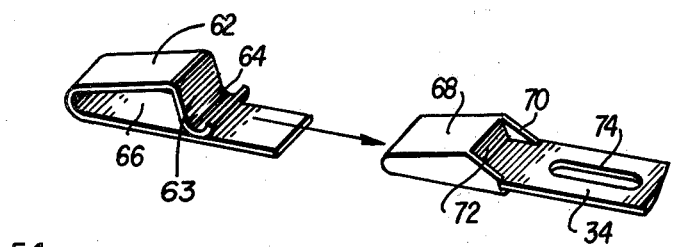
FIG. 7 is a perspective view of yet another safety disconnect device.

Referring now to FIG. 6, there is shown a tubular unit 60 having tube member 50 abutting adjustment member 51. Member 51 is preferably closed at the distal end thereof and has a threaded aperture 52 at the proximal end thereof in which is positioned adjustment screw 57. An attachment meand 55 in the end of adjustment screw 57 has loop 54 of spring 56 attached thereto. On the other end of spring 56 is loop 53 which engages attachment means 59. Attachment means 59 has an upper elongated flat portion 58 terminating in a loop portion 62 and external attachment means 64 biased against lower portion 66. It will be understood that the embodiment of the attachment means and the various portions thereof may take on different forms. The important features are those which provide attachment to spring loop 53 under tension without slipping into tube 50, and stop member 61 which prevents the spring attachment member 58 from being withdrawn from tube 50 and which provides means for activating the disconnecting mechanism 64 in case of improper or inadvertent removal of the facebow from the buccal tubes. Portion 64, or a suitable variation thereof, resiliently locks to an intermediate connecting strap 34 by engaging a hole 68 therein or other suitable engagement. Application of sufficient longitudinal force on the intermediate strap 34 will disconnect the strap 34 from the engaging member 64.

Adjustment of the tension on the facebow may be accomplished by turning member 51, thereby varying the length of adjustment screw 57 within the tube 50. A capacity for infinite tension adjustment settings, within limits of the spring 56, is thus provided. Engagement of intermediate connecting strap 34 to the outer bow member is with a series of holes 74 as more clearly shown in FIG. 3. This adjustment in relationship to the amount of tension on the spring determines the travel distance of the attachment means 59 to stop 61. Hence, a versatile and effective safe headgear force system is provided.

The invention just described provides several advantages over other spring biased tensioning systems now available. First, this device provides the orthodontist the option of choosing the amount of travel allowed before the disconnecting mechanism becomes effective. This is accomplished by engaging the appropriate hole 74 or 74' in the intermediate attachment strap 34 with the hooked end of an outer bow. Second, the force adjustment system provides an infinite number of settings, a feature not presently available on existing spring tensioning systems; presently existing systems require pre-setting at the factory with only limited force range options which must be varied in discrete increments. Third, the force adjustment can be easily made during the fitting stage while on the patient's head or around the patient's neck; the force applied is related to the number of turns applied to the adjustment member 51 and the pitch of adjustment screw 57, thereby eliminating the need for adjustment indicia.

Figure 5:
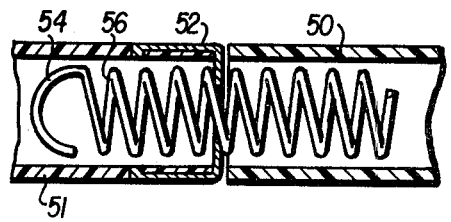
FIG. 5 is a schematic view, partially in cross-section, of a continuously variable tension adjustment device of the present invention.

FIG. 5 shows a variation of the force adjusting unit of FIG. 6. The adjustment member 51 has a large opening at the end thereof and the end walls 52 are adapted to engage directly between the coils of spring 56. By rotating member 51 in relation to tube 50, the tension of the spring can be varied in a fashion similar to that described in FIG. 6. The main advantage of this variation is that the screw member 57 of FIG. 6 can be eliminated, providing simpler and less expensive manufacture. The pitch of the spring provides the same force adjustment benefits as the apparatus of FIG. 6.

FIG. 7 shows a variation of the attachment means 59 and 64 of FIG. 6 with the corresponding intermediate attachment. This attachment variation has a flat bottom plate 66, an inclined upper plate 62, and a loop segment 63 having arcuate portion terminating in an attachment portion 64 at the end of the loop. This attachment is adapted to engage over an inclined flat section 68 on the end of strap 34 which latter has hole 74 therein. Tab portions 70 maintain the clip in place against lateral movement. When in place, arcuate portion 63 rests against surface 72. Although this type of arrangement is similar to that shown in FIG. 6, it provides some distinct advantages in that the force adjustment to insure release of the attachment can be conveniently controlled by altering the resiliency of the attachment members 62, 63 and 64, the thickness of member 68 and the angle of surface 72.

Figure 8:
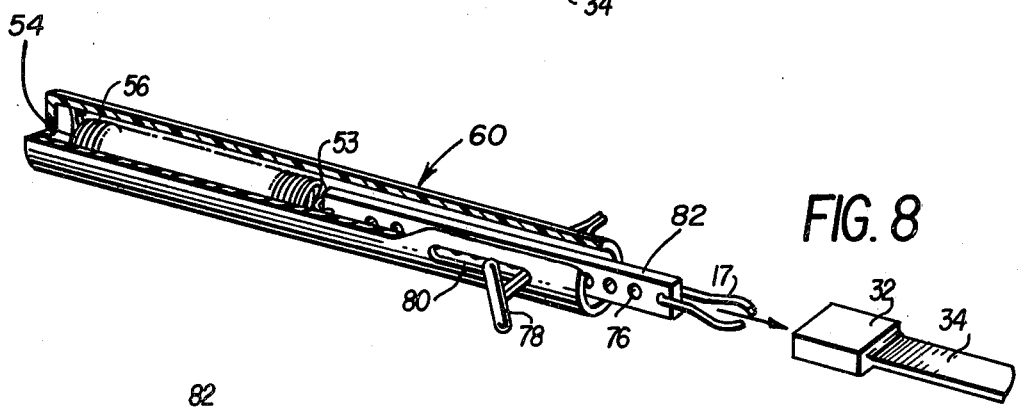
FIG. 8 is a partially cutaway perspective view of a safety release device similar to that in FIG. 3 with another variation of the tension and travel limiting means of the present invention.
Figure 9:
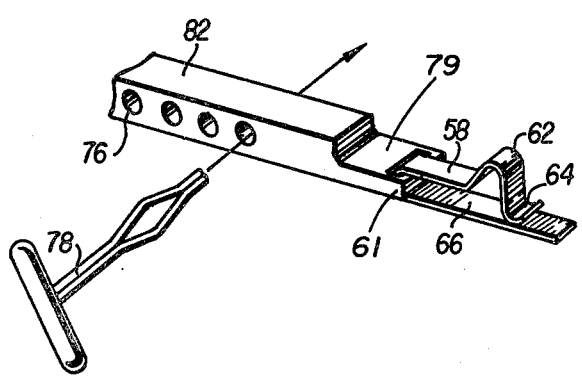
FIG. 9 is an enlarged perspective view of the travel limiting means of FIG. 8 in conjunction with a safety release device of the type shown in FIG. 6.

The devices shown in FIGS. 8 and 9 provide substantially similar benefits to that of FIG. 6 with the major differences being in the mechanisms for adjusting force and activating the disconnecting feature. In these embodiments, tensioning force is adjusted entirely by hole selection in the intermediate connecting strap 34, which is more clearly shown in FIG. 3. A pin device inserted into a hole in a linking member determines the amount of free travel permitted after force selection has been so made. Attachment and disconnecting means are similar to those of FIGS. 3 and 6. The major advantage of these pin type travel limiting systems is that a wide range of forces may be easily selected without interferring with either the attachment or disconnecting system.

FIG. 8 shows a force system arrangement designed to accomplish resilient and adjustable attachment means to bias a headgear facebow. A tubular unit 60 is provided which houses the force means and other components. The spring force means 56 is secured at one end 54; the other end 53 is connected to one of a series of holes in a link 82. A deformable compression release member 17 is securely attached to the outer end of link 82 and fits within a shaped opening in section 32 of strap 34, as shown more clearly in FIG. 3. To select the amount of travel and to limit the travel distance in order to activate the compression member disconnecting portion 17, pin 78 is withdrawn. The force is selected by attaching strap 34, using the appropriate hole in strap 34, to the facebow 26 (both shown in FIG. 3) and the pin 78 is then re-inserted. A slot 80 in the tube in cooperation with the pin 78 provides control of the length of travel within slot 80 depending upon which hole pin 78 is inserted into. Any amount of pulling force which causes pin 78 to reach the travel limit allowed by slot 80 will be transferred to deformable portion 17 which will then compress and disengage strap 34 from tubular unit 60.

FIG. 9 shows a force system arrangement which is similar to that of FIG. 8 but with a safety release mechanism similar to that shown in FIG. 6. Link 82 has adjustment holes such as 76 therein through which pin 78 is adapted to extend to ride in slot 80 as shown in FIG. 8. Extension portion 79 of link 82 is adapted to receive the attachment means 58 which is substantially the same as that shown in FIG. 6. The unit can be adapted for use with an intermediate attachment strap such as 34 in FIG. 6. Adjustment and disconnecting features can be the same as for the unit of FIG. 8.

The preceding examples can be repeated with similar success by substituting the generically or specifically described reactants and/or operating conditions of this invention for those used in the preceding examples.

From the foregoing description, one skilled in the art can easily ascertain the essential characteristics of this inventon, and without departing from the spirit and scope thereof, can make various changes and modifications of the invention to adapt it to various usages and conditions.

What is claimed is:
1. A safety orthodontic headgear tensioning system for use with an orthodontic facebow, comprising:
   a coil spring having a first end and a second end for producing the tensioning forces of the system;
   a tube having a first opening at one end and a second opening at the other end for enclosing said coil spring and intermediate connecting means, said first end located near said first opening and said second end located near said second opening, said tube having opposed elongated cutouts oriented longitudinally to the tube near the first end thereof;
   said connecting means comprising a rigid member with a plurality of holes along at least an intermediate portion thereof, one end of said member being securedly engaged to said first end of said spring and the other end being securedly engaged with a first end of a coupling means;
   said coupling means being securedly mounted to said connecting means at a first end and having opposed travel limiting resilient members at a second end; and
   means cooperating with said intermediate connecting means for limiting the expansion travel of the first end of said spring with respect to said first tube opening.
2. The headgear tensioning system of claim 1 further including disconnect means for releasably engaging said opposed resilient members by means of the compression or expansion of said members such that said opposed members will disengage from said disconnect means when stressed beyond a predetermined amount.
3. The headgear tensioning system of claim 1 wherein said elongated cutouts, said intermediate connecting means and said travel limiting means together comprise means for selecting the allowable travel distance of said spring.
4. The headgear tensioning system of claim 1 wherein said spring, said travel limiting means, said releasable coupling means and said tube comprise a self-contained unit for biasing intraoral orthodontic devices.
5. The headgear tensioning system of claim 1 wherein said travel limiting means includes a travel limiting pin releasably engaging said intermediate connecting member.
6. The headgear tensioning system of claim 1, wherein said travel limiting means comprises a pin for selective insertion in any of the apertures in said connector, said pin extending through at least one of said cutouts.
7. The headgear tensioning system of claim 6 wherein said pin is inserted into the intermediate connecting means through said elongated holes after tension is applied to said spring so that said spring will be prestressed to a predetermined amount.
8. The headgear tensioning system of claim 1, wherein said disconnect means comprises an intermediate attachment strap securely fastened to an outer bow or other intraoral applying device at one end and having its opposite end suitably adapted to releasably engage the said resilient coupling member.
9. The headgear tensioning system of claim 8 wherein said connecting strap includes a plurality of holes for adjustable attachment to said outer bow or other intraoral force applying device.

* * * * *